US006819957B1

(12) United States Patent
Le (10) Patent No.: US 6,819,957 B1
(45) Date of Patent: Nov. 16, 2004

(54) ELECTRICAL STIMULATION APPARATUS AND METHOD

(75) Inventor: Tuan Vinh Le, 3695 Kaneff Crescent, Suite 2006, Mississauga, Ontario (CA), L5A 4B6

(73) Assignee: Tuan Vinh Le, Mississauga (CA)

( * ) Notice: Subject to any disclaimer, the term of this patent is extended or adjusted under 35 U.S.C. 154(b) by 251 days.

(21) Appl. No.: 09/941,311

(22) Filed: Aug. 29, 2001

(51) Int. Cl.[7] ............................................. A61N 1/18
(52) U.S. Cl. ........................... 607/62; 607/46; 607/48; 128/905; 128/907
(58) Field of Search ............................. 607/46, 48, 115, 607/138, 148, 1, 2, 42, 44, 62; 128/905, 907

(56) References Cited

U.S. PATENT DOCUMENTS

| | | | |
|---|---|---|---|
| 4,023,574 A | 5/1977 | Nemec | |
| 4,037,332 A | 7/1977 | Petrusinsky | |
| 4,596,251 A | 6/1986 | Plicchi et al. | |
| 4,712,558 A | 12/1987 | Kidd et al. | |
| 4,917,092 A | 4/1990 | Todd et al. | |
| 5,048,523 A | 9/1991 | Yamasawa et al. | |
| 5,199,442 A | 4/1993 | Seager et al. | |
| 5,304,207 A | 4/1994 | Stromer | |
| 5,344,386 A | 9/1994 | Schaldach | |
| 5,350,414 A | 9/1994 | Kolen | |
| 5,540,736 A | 7/1996 | Haimovich et al. | |
| 5,607,461 A | 3/1997 | Lathrop | |
| 5,823,913 A | 10/1998 | Aruin et al. | |
| 5,891,182 A | 4/1999 | Fleming | |
| 5,979,456 A | 11/1999 | Magovern | |
| 5,988,171 A | 11/1999 | Sohn et al. | |
| 6,055,452 A | 4/2000 | Pearlman | |
| 6,212,435 B1 * | 4/2001 | Lattner et al. | 607/42 |
| 6,463,327 B1 * | 10/2002 | Lurie et al. | 607/42 |
| 6,651,652 B1 * | 11/2003 | Ward | 607/42 |

OTHER PUBLICATIONS

Dr. Ho's Double Muscle Massage System Unit, http://www.drhonow.com/dualunit.htm, Jul. 10, 2001, 3 pages enclosed.

* cited by examiner

Primary Examiner—George R. Evanisko
(74) Attorney, Agent, or Firm—Ridout & Maybee LLP

(57) ABSTRACT

An electrical stimulation device for applying electrical stimulation to living tissue, including a plurality of electrode pairs adapted to be applied along a spinal area of a person, a sensing device for sensing breathing of the person, and a controller connected to receive signals from the sensing device and control operation of the electrode pairs, the controller being configured to, based on signals received from the sensing device, cause the electrode pairs to apply stimulating electrical pulses to areas of the person to which they are respectively applied.

13 Claims, 6 Drawing Sheets

ELECTRICAL STIMULATION APPARATUS AND METHOD

BACKGROUND OF THE INVENTION

This invention is directed towards an electric nerve or muscle stimulator, and in particular a stimulator that is controlled based on detected breathing patterns.

Recent years have seen a rise in interest in western countries in alternative therapies such as meditation, acupressure, and acupuncture, that have been practised in eastern cultures for thousands of years. Interest in more contemporary variations of alternative therapies such as electrical muscle and nerve stimulation has also soared in recent years, resulting in a proliferation of transcutaneous electric stimulation devices appearing on the market.

Numerous branches of medicine deal with the stimulation of the body's nervous system. Traditional Chinese acupuncture is based on the proposition that stimulation of specific areas on the skin affects the functioning of certain organs of the body and can balance energy levels in the body. It has evolved into a system of medicine that is believed by many to restore and maintain health by the insertion of fine needles into acupuncture points just beneath the body surface that lie on channels of energy. Small electric currents may also be used in the place of fine needles. In Western medicine, sending an electrical impulse to selected nerve fibres in the spinal cord (spinal cord stimulation) is used to block pain messages from the spinal cord to the brain.

Breathing efficiently has been shown to improve and promote health and personal well-being. Meditation and Tai Chi both use breathing methods that are intended to focus the mind and promote deep-relaxed breathing. It has been observed that meditation leads to a "relaxation response" resulting in changes in the body that are deeply restorative and which quicken healing. These changes include reductions in heart rate, blood pressure, respiratory rate, oxygen consumption, blood flow to skeletal muscles, perspiration and muscle tension, as well as an improvement in immunity. Some eastern doctrines, for example Taoism, rely on a combination of breath control and exercise to achieve a healthy mind and body by stimulating energy flow through the body. Some experienced and highly trained practitioners of meditation use stimulation of muscles and or nerves below the base of the spine (for example, the rectal sphincter muscle) and along the back at appropriate times during the meditative breathing cycle to balance energy flow through the body resulting in further promotion of the benefits of meditation. In the past, the stimulation has been done by the person meditating manually clenching or activating selected muscles at certain times during his or her meditative breathing cycle. This requires the person performing the meditation to be highly trained and motivated in order to coordinate their breathing and muscle activity to achieve maximum benefits.

It is therefore desirable to provide a method and device that reinforces proper meditative breathing and that assists a person in stimulating selected muscles or nerves during his or her breathing cycle.

SUMMARY OF THE INVENTION

The present invention provides an electrical stimulation device including a breathing pattern detector and electrodes to stimulate selected tissues of a user in coordination with the user's breathing pattern. Electrical stimulation is preferably performed at the anal area and along the spine of the user at selected times during each breathing cycle in order to assist in promoting relaxation and a feeling of well-being.

According to one aspect of the invention, there is provided an electrical stimulation device for applying a stimulation signal to living tissue. The device includes a sensor for sensing breathing of a person, at least a first electrode pair and a second electrode pair for contacting the living tissue of the person, and a controller responsive to the sensor and operatively connected to the first electrode pair and the second electrode pair. The controller is configured to determine a breathing cycle pattern of the person based on input from the sensor and cause the first electrode pair and the second electrode pair to apply a stimulating first waveform signal and second waveform signal, respectively, to the living tissue based on the determined breathing cycle pattern of the person. Preferably, the controller is configured to cause the first electrode pair and the second electrode pair to apply the first waveform signal and the second waveform signal, respectively, to the living tissue for predetermined durations during each determined breathing cycle of the person during a treatment period, the second waveform signal commencing a predetermined delay after commencement of the first waveform signal in each breathing cycle. As well, the first electrode pair is preferably adapted to be applied to an anal area of the person, and the second electrode pair is adapted to be applied higher than the first electrode pair to a lower spine area of the person.

According to a further aspect of the present invention, there is provided a method for applying a stimulation signal to living tissue that includes: (a) monitoring the breathing pattern of a person; and (b) applying stimulating electrical waveforms signals to the anal area of the person in response to the monitored breathing pattern. According to yet a further aspect of the invention, there is provided a method for applying a stimulation signal to living tissue that includes (a) monitoring the breathing pattern of a person; and (b) applying stimulating electrical waveforms signals to the spinal area of the person in response to the monitored breathing pattern.

According to still a further aspect of the invention there is provided an electrical stimulation device for applying electrical stimulation to living tissue, including a plurality of electrode pairs adapted to be applied along a spinal area of a person, a sensing device for sensing breathing of the person, and a controller connected to receive signals from the sensing device and control operation of the electrode pairs, the controller being configured to, based on signals received from the sensing device, cause the electrode pairs to apply stimulating electrical pulses to areas of the person to which they are respectively applied.

Other aspects and features of the present invention will become apparent to those ordinarily skilled in the art upon review of the following description of specific embodiments of the invention in conjunction with the accompanying figures.

DISCLOSURE OF THE PREFERRED EMBODIMENTS

Figure 1:
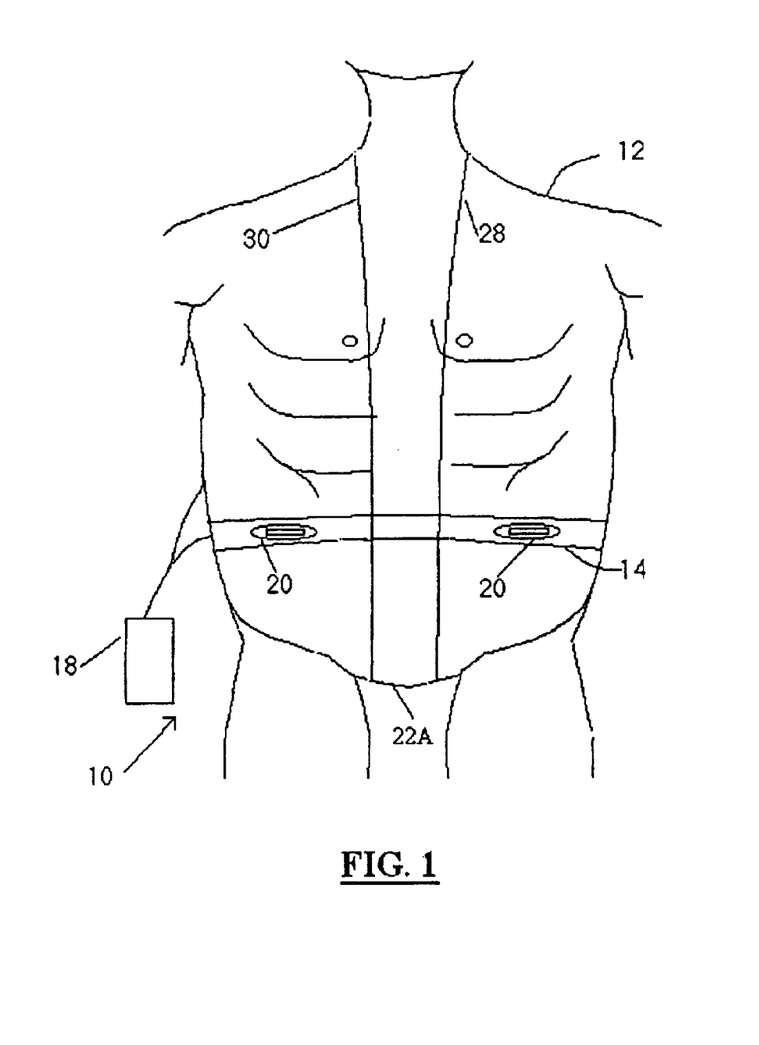
FIG. 1 is a partial front view showing a person wearing an electrical stimulation device according to embodiments of the present invention.
Figure 2:
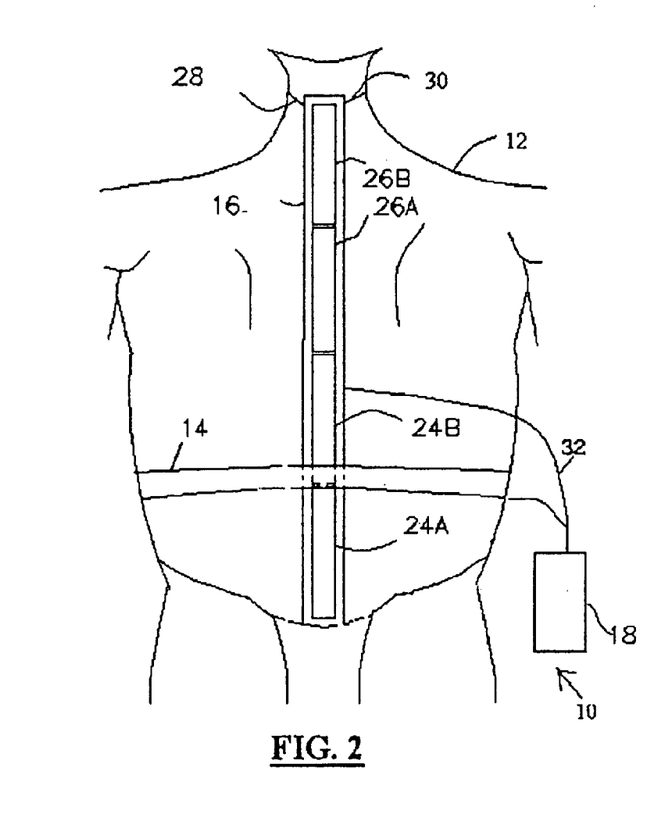
FIG. 2 is a partial back view of a person wearing the electrical stimulation device of FIG. 1.
Figure 3:
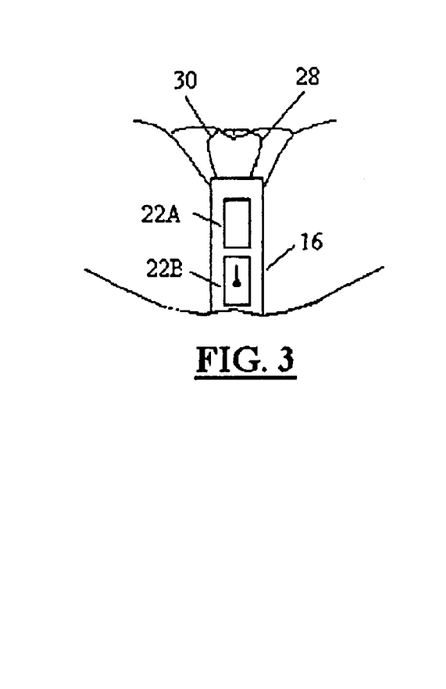
FIG. 3 is a partial bottom view of the person wearing the electrical stimulation device of FIG. 1.

With reference to FIGS. 1–3 an electric stimulation device 10 in accordance with preferred embodiments of the invention is shown mounted on a person 12. The electric stimulation device 10 includes a sensor belt 14, an electrode belt 16 and a control unit 18. The sensor belt 14 is provided and formed of any suitable flexible and resilient material and can be adjusted to fit the user's torso size. As an illustrative example, the sensor belt 14 may preferably be designed as an elastic or non-elastic belt and may be of any desired adjustable length which will fit both men and woman (for example from 30 inches to 65 inches). Also, the sensor belt 14 may be of any suitable or desired construction and material and may have any suitable closure or buckle to allow easy installation of the sensor belt about the person's torso. Attached to the sensor belt are two sensor units 20. Each of the senor units 20 include a pressure sensitive switch that closes when a sufficient amount of pressure is applied thereto. The pressure mounted switch can be mounted in a sensor housing which can be secured by adhesive or velcro (TM) hook and loop like material positioned on the sensor housing and the sensor belt 14, thereby permitting the position of the sensor units 20 to be adjusted on the sensor belt 14. In use, the two sensor units 20 are preferably positioned such that one of the sensor units 20 is located toward one side of the abdomen and the other sensor unit 20 is located towards another side of the abdomen of the user 12. The pressure sensitive switches of the sensor units 20 are directed inwards towards the person 12 such that movement of the person's abdomen in an outward direction will cause the pressure switches located within the sensor units 20 to close, and subsequently open upon retraction of the abdomen of the person 12. The sensor units 20 are electrically connected to the control unit 18 such that the control unit 18 can detect whether one or both of the pressure switches associated with the sensor unit 20 are closed and/or open.

The electrode belt 16 preferably includes three pairs of treatment electrodes including a first "anal zone" pair of electrodes 22A, 22B, a second "lower back zone" pair of electrodes 24A and 24B and a third "upper back zone" pair of electrodes 26A, 26B. The treatment electrodes are each preferably formed from flexible material having a conductive grid embeded therein for transferring electrically energy from the electrodes to the human body. The conductive surfaces of each of the electrodes may have a conductive gel pad affixed thereto to assist securing the electrodes to the person 12 and also to increase conductivity between the electrodes and the skin of the person 12.

As illustrated in FIGS. 1–3, in a preferred embodiment the three electrode pairs are longitudinally positioned along the elongate electrode belt 16 so that they can be positioned on the person 12 with the first pair of electrodes 22A, 22B being located at the anal area of the person 12, the second pair of electrodes 24A, 24B can be located along a longitudinal spinal area above the first electrode pair 22A, 22B, and the third electrode pair 26A, 26B can be positioned along an upper spinal area above the second electrode pair 24A, 24B. The electrode belt 16 includes straps 28 and 30 which extend from an upper portion of the belt located near the top electrode 24B to a lower part of the belt located near the front of electrode 22A in order to assist in fastening the electrode belt 16 to the body of the person 12. The straps 28 and 30 are intended to extend from the belt to pass around opposite sides of the neck of the person 12, extend down the front of the body of the person, and connect in the crotch area to a bottom portion of the electrode belt 16. The straps 28 and 30 are preferably adjustable in length and include a buckle or other realeasable closure means to enable the electrode belt 16 to be removed from the body of the person 12.

Although the electrodes 22A–26B are illustrated as being fastened along a belt, the electrodes could alternatively each be physically separated from each other and individually placed on the body of the person 12 in the locations indicated in the figures. Positioning the electrodes along the electrode belt 16 offers an advantage however in that it assists in securing the electrodes to the body of the person 12, and furthermore assists in achieving the correct electrode ordering and positioning along the spine and lower spine areas of the person 12. Each of the electrode pairs 22A–B, 24A–B and 26A–B are electrically connected through a multiple conductor cable 32 to the control unit 18. In a preferred embodiment, each of the electrode pairs is arranged so that adjacent pairs have alternating polarity in order to minimize electrical interference between the electrodes. For example, electrodes 22B and 24A are both positive electrodes, and electrodes 24B and 26A are both negative electrodes.

Figure 4:
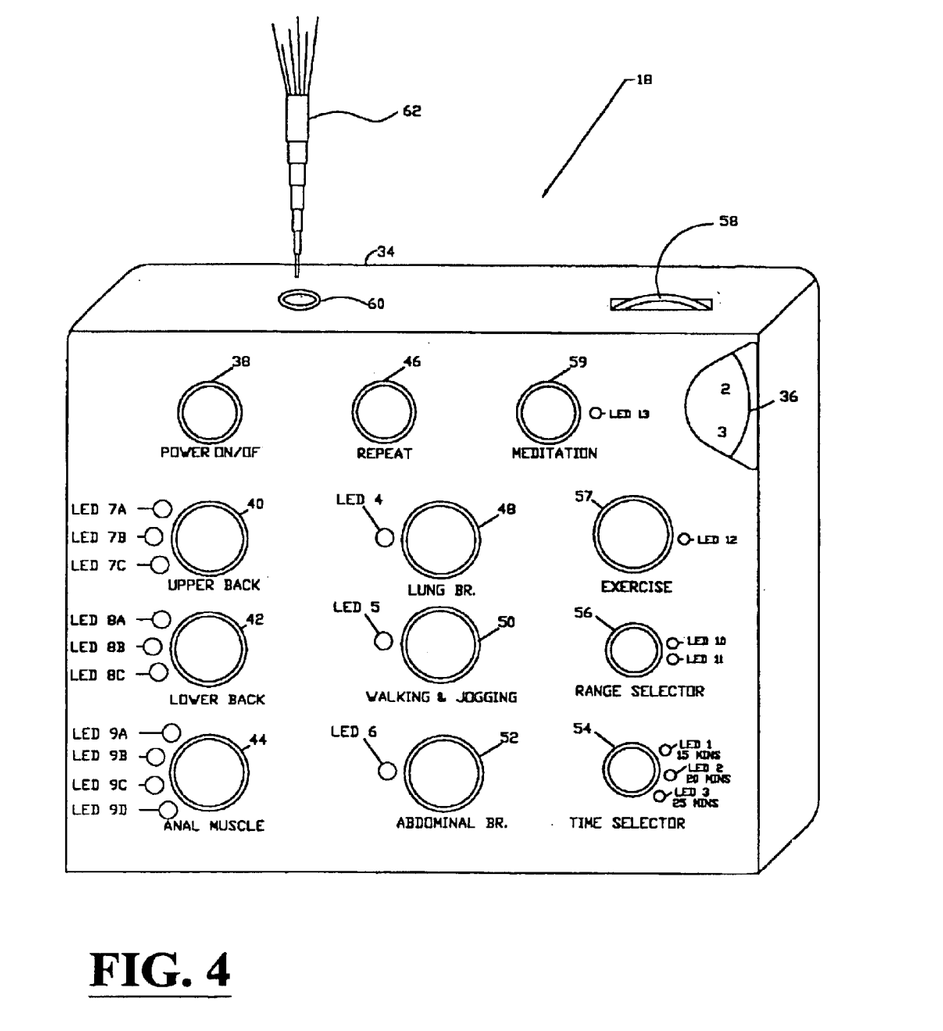
FIG. 4 is a perspective view of a preferred embodiment of an electrical stimulation controller of the electrical stimulation device of the present invention.

Turning to FIG. 4, the control unit 18 includes a circuit that is housed within a housing 34. A female connector 60 is provided for receiving male connector 62 from which a number of conductive wires extend to the sensors 20 and electrodes 22A–26B. The control unit 18 includes a master power on/off switch 38 for turning the control unit 18 on and off, an upper back switch 40 for adjusting the intensity of the signal provided to the upper back zone electrode pair 26A, 26B; a lower back switch 42 for adjusting the electrode intensity to the lower back zone electrode pair 24A–24B; and an anal muscle switch 44 for adjusting the signal provided to the anal zone electrode pair 22A–22B. A repeat switch 46 is provided to allow restarting of another timed cycle using the settings recorded for the previous timed cycle.

In one preferred embodiment, a lung breathing mode switch 48, jogging and walking mode switch 50, abdominal breathing mode switch 52, exercise mode switch 58 and mediation mode switch 59 are provided for selecting between five different modes of operation for the electric stimulation device 10, as will be explained in greater detail below. A time selector switch 54 is provided to allow a user to select between one of three different possible treatment time durations, the selected length of which is indicated by visual indicator. In the embodiment shown in FIG. 4, a first display element LED 1 lights up if the selected time is 15 minutes, a second display element LED2 lights up if the selected time is 20 minutes, and a third display element LED3 lights if the selected treatment time is 25 minutes. Display elements LED4, LED5, LED6, LED12 and LED13 are located next to the lung breathing mode switch 48, jogging and walking mode switch 50, abdominal breathing mode switch 52, exercise mode switch 57, and mediation mode switch 59, respectively, to provide a visual indication of which of these five possible modes has been selected by the user. Three display elements LED7A–LED7C are located next to the upper back switch 40 to provide a visual indication of which of three possible intensity levels have been selected by the user in respect of the upper back zone electrode pair 26A–26B. Similarly, three display elements LED8A–LED8C are positioned next to lower back switch 42 and four display elements LED9A–LED9D are positioned next to anal muscle switch 44 to indicate the different intensity levels that have been selected by such switches for the electrode pairs 24A–B and 22A–B, respectively. A thumbwheel 58 is provided as a master intensity selector to allow the user to adjust the maximum desired strength of signal supplied to all three pairs of electrodes. The wheel 58 may have the indicia 1–5 printed on an outer surface thereof and visible through a window 36 in the housing to provide an indication to the user of the maximum intensity level that has been selected. A range selection switch 56 is provided for use in conjunction with intensity selection switches 40, 42 and 44, and thumbwheel for adjusting the signal intensity applied to the electrode pairs. Two display elements LED10A and LED10B are provided to indicate which of two possible intensity ranges are selected, with LED10A indicating a "low" range and LED10B indicating a "high" range.

Figure 5:
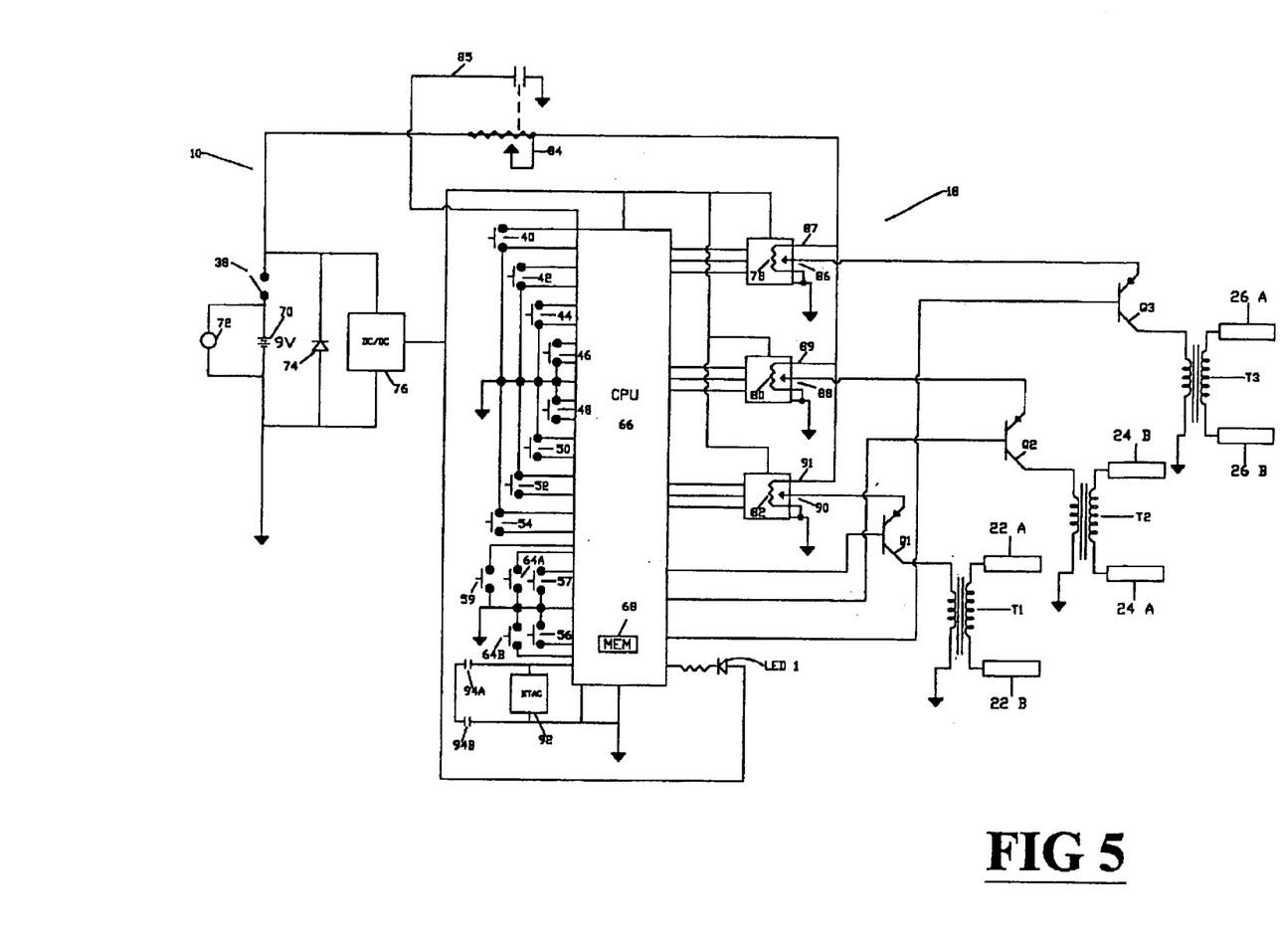
FIG. 5 is a schematic diagram of a preferred embodiment of the electronic stimulation device of the present invention.

Referring now to FIG. 5, there is shown a partially block, partially schematic diagram of the electric stimulation device 10 according to preferred embodiments of the instant invention. The data processing functions of the instant invention are performed by a microcomputer or CPU 66 which is, preferably, a single integrated circuit data processing chip. In a preferred embodiment, the CPU 66 includes memory 68. The memory 68 can take the form of an electrically erasable, programable, read-only memory (EE prom). While not limited thereto, the CPU 66 is preferably a stand alone, high performance single chip micro-controller fabricated in plus 5 volt advanced CMOS technology so as to provide low power consumption along with high speed operation. The memory 68 is used by the CPU 66 for a storage of the application specific instructions required for the functionality of the present invention as described herein.

The electric stimulation device 10 is powered by a rechargeable 9 volt nickel-cadmium battery 70. An external DC voltage obtained from an external AC/DC converter (120 VAC to 9VDC) can be applied to a jack 72 to recharge the battery 70, or alternatively act as the power supply for the electric stimulation device 10. A diode 74 placed in parallel with the battery 70 protects against damage to the battery resulting from incorrect polarity of power applied to jack 72. Master Power on/off switch 38 is connected in series with the batter 70. A DC to DC converter 76 is used to convert the 9 volt power supply to a usable 5 volt DC logic voltage VCC. The 5 volt VCC is supplied to the CPU 66, digital potentiometers 78, 80 and 82 and the 19 status display elements LED1–LED12. (For the purpose of simplifying the diagram on FIG. 5, only one display element LED1 is shown. However, the 19 additional LEDs are each individually connected to the CPU 66 in a manner similar to display element LED1.)

The 9 volt source is connected through a manually actuated potentiometer 84 to supply power to the resistor portions of each of the digital potentiometers 78, 80 and 82. The value of the manual potentiometer 84 is controlled by thumbwheel 58 and determines the maximum intensity of the signal that can be provided to the respective signal input terminals 87, 89 and 91 of each of the digital potentiometers 78, 80 and 82. A sensor input 85 from the potentiometer 84 is provided to the CPU 66 so that the CPU 66 can track the potentiometer setting (and hence the position of thumbwheel 58). The switches 40 to 57 and 59 are all electrically connected to the CPU 66 such that the CPU 66 can determine when such switches have been depressed. Similarly, pressure switches 64A and 64B, each of which is located within a respective sensor unit 20, are electrically connected to the CPU 66 such that the CPU 66 can determine when one, or the other, or both of the sensor pressures switches 64A or 64B are closed or open. The CPU 66 is operatively connected to each of the digital potentiometers 78, 80 and 82 so that the CPU 66 controls the tap location in each of the respective potentiometers 78, 80 and 82. Thus, while manual potentiometer 84 (which is adjusted by the thumbwheel 58) dictates the maximum voltage of the signal that can be applied to input terminals 87, 84 and 91 of the digital potentiometers 78, 80 and 82, the CPU 66 controls what proportion of the maximum voltage is actually output on the output terminals 86, 88 and 90 of the potentiometers.

The output terminal 90 of the digital potentiometer 82 is connected to supply power to the anal zone electrode pair 22A–22B via a transistor Q1 and an isolation transformer T1. The output terminal 88 of digital potentiometer 80 is connected to supply power to the lower back zone transistor pair 24A–24B via transistor Q2 and isolation transformer T2, and similarly the output terminal 86 of digital potentiometer 78 is connected to supply power to the upper back electrode pair 26A–26B via a transistor Q3 and isolation transformer T3. The base of each of the transistors Q1, Q2 and Q3 is connected to the CPU 66 such that the CPU 66 can turn each of the transistors Q1, Q2 and Q3 selectively on and off in accordance with predetermined patterns to permit signal pulses to be output from the respective electrode pairs. Accordingly, the frequency and duration of the signals output by the respective electrode pairs is controlled by the CPU 66 gating of transistors Q1, Q2 and Q3. The amplitude of the signals output by the electrode pairs is controlled by adjustment of the digital potentiometers 78, 80 and 82 by the CPU 66, with the maximum amplitude of the output signals being determined by the position of manually adjusted tap 84.

The isolation transformers T1, T2 and T3 are sized to convert the voltages provided by transistors Q1, Q2 and Q3 to a final desired output level. In one embodiment, the transformers T2 and T3 are sized to provide a maximum output voltage of 20 volts, and the isolation transformer T1 has a turns ratio to provide 50% of that value, namely 10 volts, based on a maximum 9 volt input signal.

A piezoelectric crystal 92, together with capacitors 94A and 94B provides a stable frequency source for the operation of the time and control functions of the CPU 66.

An overview of the various components of the stimulation device 10 having been provided, its operation will now be explained in greater detail. During operation, the control unit 18 is configured to apply stimulating pulses to each of the electrode pairs 22A–22B, 24A–24B and 26A–26B for predetermined intervals during each breathing cycle of the person using the device. The timing of the predetermined intervals within each breathing cycle and the length of the predetermined intervals depends on which one of the five possible modes have been selected by the user through activation of the lung breathing mode switch 48, the jogging and walking mode switch 50, the abdominal breathing mode switch 52, the exercise mode switch 57 or the mediation mode switch 59. The treatment time that the device operates continuously for is selected by the user using time selector switch 54, which in the illustrated embodiment allows for three different run times, namely 15, 20, and 25 minutes. The selected treatment time is identified by a corresponding visual indicator LED1, LED2 and LED3. A maximum pulse intensity for the three electrode pairs is determined by the setting of the thumbwheel 58 and the range that has been selected by the range selector switch 56. In particular, the CPU 66 is configured to allow the digital potentiometers 78, 80 and 82 to output signals within two possible ranges, namely a "high" range and a "low" range, as selected by the range selector switch 56. The default is "low" range, and when such range is selected, the CPU 66 will only allow the digital potentiometers 78, 80 and 82 to output up to a maximum of 50% of the signal intensity applied to their respective input terminals 87, 89 and 91. If the CPU 66 detects that the range selection button 56 is pressed twice in quick succession at the same time that the thumbwheel 58 is positioned at its lowest intensity setting "1", it will place the control unit 18 into a "high" range in which the CPU 66 will allow the digital potentiometers to output between 50 to 100% of the signal intensity applied to their respective input terminals 87, 89 and 91. In one embodiment, the control unit 18 will, once "high" range has been selected, continue to operate in high "range" until the user moves the thumbwheel out of then back into its lowest intensity "1" setting, or the control unit is turned off. Thus, the setting of thumbwheel 58, and the range selected by range selector 56 determines the maximum pulse intensity that can be applied to each of the electrode pairs. Within either the "high" or "low" ranges, a percentage of the maximum pulse intensity applied to the electrode pairs is individually determined for each pair by the corresponding upper back switch 40 (for the upper back zone electrode pair 26A–26B), lower back switch 42 (for the lower back zone electrode pair 24A–24B), and anal muscle switch 44 (for the anal zone electrode pair 22A–22B). In particular, the switches 40 and 42 each allow for three different intensity levels to be selected, namely 70%, 85% and 100% of the maximum pulse intensity as determined by the thumbwheel 58 and range selector switch 56. Visual indicators LED7 and LED8 indicate what intensity level has been selected by switches 40 and 42 respectively. As the anal area tends to have a greater degree of sensitivity, the anal muscle switch 44 allows for four different intensity levels to be selected, namely 70%, 80%, 90% or 100% of the possible maximum intensity value. As noted above, the isolation transformer associated with the anal zone electrode pair 22A–22B is, in one embodiment, sized such that the maximum pulse intensity for the anal zone electrode pair is half that of the lower and upper back zone electrode pairs 24A–24B and 26A–26B.

The inclusion of the range selection switch is of course an optional embodiment of the invention, however its presence ensures that the user of the device 10 has actively decided to use the higher intensity voltages, rather than mistakenly selected a higher intensity.

In one embodiment of the invention, the control unit 18 is configured so that the electrical pulses provided to the lower and upper back zone electrode pairs 24A–24B and 26A–26B can have a maximum voltage amplitude of up to 10V in "low" range, and a maximum current of 11 mA, and a maximum voltage of 20 v in "high" range and a maximum current of 18 mA. The electrical pulses provided to the anal zone electrode pair have half the voltage values note above. The voltages and currents provided above are merely illustrative.

Figure 6:
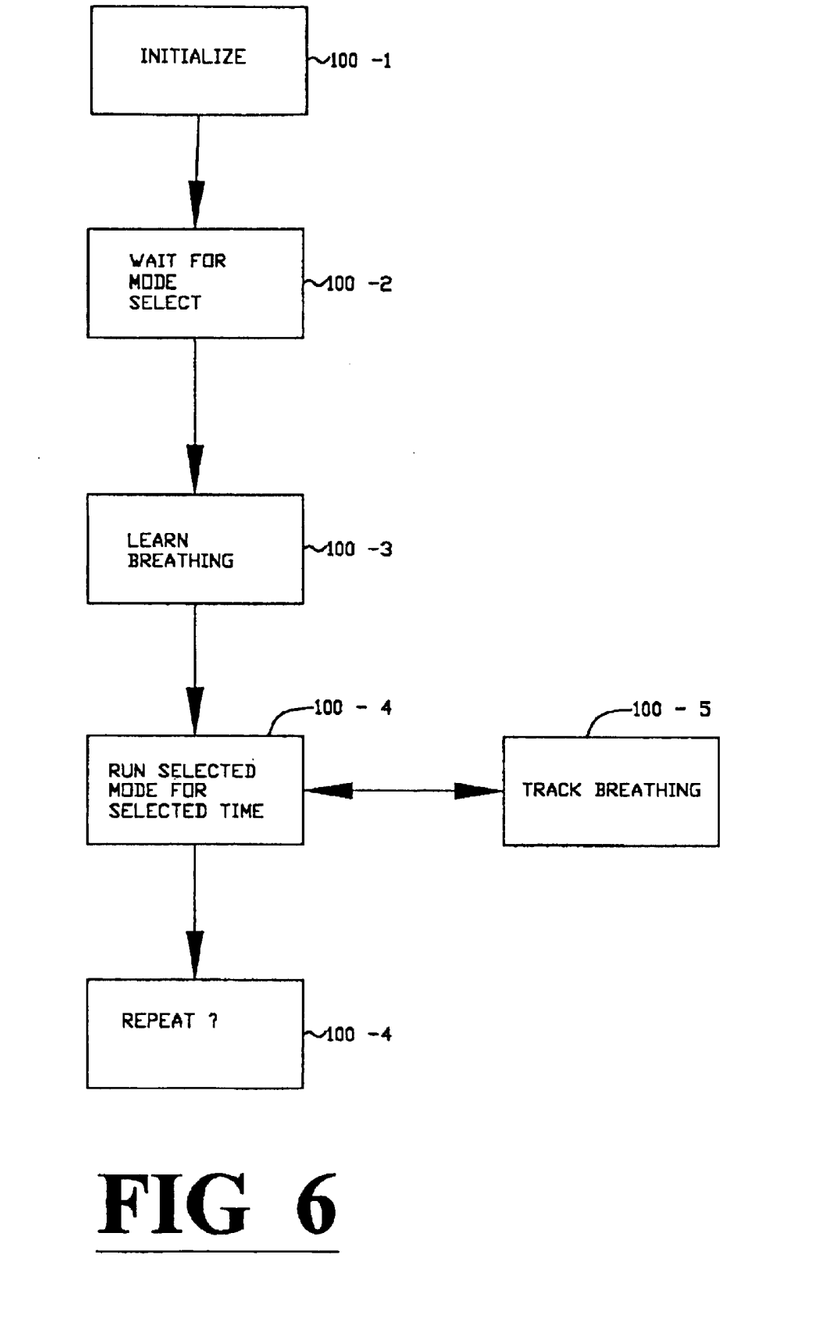
FIG. 6 is a flowchart of the operation of the electric stimulation device in accordance with embodiments of the present invention.

The power on/off switch 38 is used to activate the stimulation device 10. The flowchart 100 of FIG. 6 is illustrative of the operation of one embodiment of the stimulation device 10 once it has been turned on. When first turned on, the CPU 66 performs an initialization routine (step 100-1) during which it is reset and configured to select as default values the lowest intensity values for the anal muscle zone, lower back zone and upper back zone electrode pairs, and the lowest operating time duration (15 minutes in the illustrated embodiment). The stimulation device 10 will not commence pulsing operation until the user selects an operating mode by pressing one of the mode selection switches 48, 50 or 52 at the same time that the thumbwheel 58 is set to its lowest intensity "1" (step 100-2). The first time a user selects an operating mode after the device 10 has been turned on, the control unit 18 will execute a "learn breathing" routine (step 100-3) during which the CPU 66 monitors input from the pressure switches 64A and 64B to determine a breathing pattern for the user (person 12). In particular, the CPU 66 monitors the operation of the pressure switches 64A and 64B over a number of breathing cycles of the person to determine an approximate breathing pattern of the person. In one preferred embodiment of the invention, the device 10 is used in conjunction with a controlled breathing pattern, with the person 12 receiving pre-use instructions, perhaps in the form of printed or video materials provided with the device 10, on the desired breathing techniques for each of the different modes of operation of the stimulation device 10.

Figure 7:
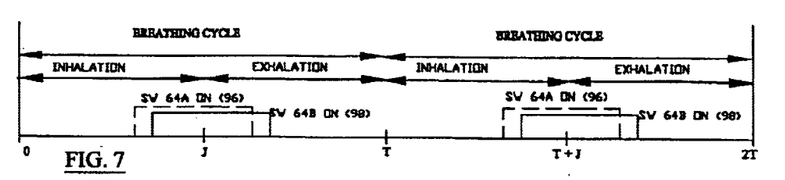
FIG. 7 is an illustrative timing diagram showing operation of sensor switches of the electrical stimulation device.

For the purpose of better explaining the operation of the present invention, FIG. 7 is an illustrative timing diagram showing possible operation of the switches 64A and 64B during the breathing cycle of the person 12. A single breathing cycle commences when the person 12 starts inhaling, and concludes when the person 12 stops exhaling. In FIG. 7, the operation of switches 64A and 64B over two complete breathing cycles is represented, with each breathing cycle having a duration of T seconds, with inhalation lasting J seconds, and exhalation lasting T–J seconds. At some point during inhalation, the pressure switches 64A and 64B will close as a result of the pressure applied to them due to the expansion of the torso of the person 12, and at some time during exhalation, the pressure switches 64A and 64 B will subsequently open back up due to contraction of the torso of the person 12. The time that the switches 64A and 64B are closed, or "on" during the two breathing cycles (illustrated in FIG. 7 by the lines 96 and 98 respectively), and the time that they are open is monitored by the CPU 66 over a number of breathing cycles during the learn breathing routine. In one embodiment, the CPU 66 is configured to perform the learn breathing routine (step 100-3 of FIG. 6) for a predetermined time period such as two minutes. Alternatively, the CPU 66 could be configured to perform the learn breathing routine until it detects that the person 12 has, within predetermined variance thresholds, maintaining an consistent breathing rate over a predetermined number of breathing cycles (for example, five breathing cycles). At the conclusion of the learn breathing routine, the CPU uses the information obtained from the two sensor switches 64A and 64B to determine, with reasonable accuracy, the average breathing cycle timing of the person 12, including breathing cycle duration, inhalation start and end timing, and exhalation start and stop timing. Although FIG. 6 illustrates the pressure switch 64A as closing prior to the pressure switch 64B during each breathing cycle, it will be appreciated that the relative timing of the switches will depend on their location on the person 12.

In some embodiments of the invention, activation of both switches 64A and 64B is required for the CPU 66 to conclude that a breathing cycle is in process. In another embodiment, the CPU 66 is configured to detect a breathing cycle upon the activation of either one of the switches 64A and 64B, thus allowing detection of breathing cycle even if one of the sensors is not activated during a particular breathing cycle due to the position of the user's body.

Once the initial learn breathing routine has been successfully completed, the control unit 18 will commence sending pulses to the three electrode pairs in accordance with the selected mode of operation for the duration of the run time as selected by the user through time selector 54 (step 100-4). In addition to determining the person's 12 breathing pattern during the initial learn breathing routine, the CPU 66 continuously tracks the person's breathing (step 100-5) throughout the ongoing operation of the device 10 in order to detect and compensate for on-going variations in the person's breathing pattern during use. In one embodiment, the CPU 66 is configured to calculate new average breathing cycle timing values at predetermined intervals based on values taken during a predetermined preceding time interval. For example, the CPU 66 could be configured to calculate new average values every minute based on average readings taken over the pervious two minutes. Preferably, the CPU 66 is configured to detect and ignore false triggering of the switches 64A and 64B that may occur, for example, from a sudden movement of the person 12. In this regard, the CPU may be configured to ignore, after the initial learn breathing routine, sporadic triggering of the switches 64A and/or 64B that occurs outside of a predetermined time window for expected switch activity. Alternatively or additionally, the CPU 66 could be configured to ignore new calculated average timing values that vary more than a predetermined amount from the previous calculated average timing values, and continue using the old values.

Figure 8:
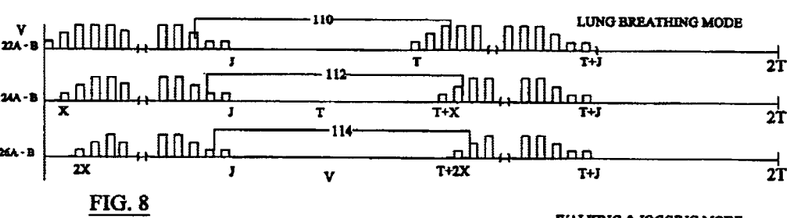
FIG. 8 is a graph showing stimulation signals generated by the electrical stimulation device during a first mode of operation in accordance with embodiments of the present invention.

FIG. 8 is illustrative of the voltage waveforms applied to the three electrode pairs 22A–22B, 24A–24B and 26A–26B during step 100-4 in the event that "lung breathing mode" has been selected by the user. In lung breathing mode, the control unit 18 is configured to apply a low frequency voltage pulse waveform to each of the electrode pairs for predetermined durations during the inhalation portion of the breathing cycle (in FIG. 8, inhalation occurs during the duration 0 to J for one breathing cycle, and duration T to T+J for the subsequent breathing cycle). In particular, the CPU 66 is configured to, at the calculated inhalation start time of the person 12, start pulsing the gate of the transistor Q1 that is associated with the anal zone electrode pair 22A–22B to cause stimulating electrical pulses to be applied through the anal zone electrode pair 22A–22B to the anal zone area of the person 12, as indicated by illustrative waveform 110. The CPU 66 is configured to continue sending the pulses to the electrode pair 22A–22B throughout inhalation and then cease at the start of the exhalation portion of the breathing cycle.

As indicated in FIG. 8, the CPU 66 is configured to start pulsing, at a predetermined delay (x) after commencing pulsing of the anal zone electrode pair 22A–22B, the gate of the transistor Q2 that is associated with the lower back electrode pair 24A–24B to cause stimulating electrical pulses to be applied through the lower back zone electrode pair 24A–24B to the lower back/spine area of the person 12, as illustrated by the waveform 112. The CPU 66 is configured to continue sending the pulses to the electrode pair 24A–24B throughout the rest of the inhalation portion and then cease at the start of the exhalation portion of the breathing cycle. The CPU 66 is also configured to start pulsing, at a predetermined delay (x) after commencing pulsing of the lower back zone electrode pair 24A–24B, the gate of the transistor Q3 that is associated with the upper back electrode pair 26A–26B to cause stimulating electrical pulses to be applied through the upper back electrode pair 26A–26B to the upper back/spine area of the person 12, as illustrated by the waveform 114. The CPU 66 is configured to continue sending the pulses to the electrode pair 26A–26B throughout the rest of the inhalation portion and then cease at the start of the exhalation portion of the breathing cycle.

Thus, in lung breathing mode, during each breathing cycle, the anal zone electrode pair 22A–22B is activated commencing at the start of inhalation, followed after a predetermined delay by the lower back electrode pair 24A–24B, followed after a further predetermined delay by the upper back electrode pair 26A–26B, with stimulating pulses from all three electrode pairs continuing through the remainder of inhalation and ceasing at the start of exhalation, with the inhalation and exhalation start times being determined by the CPU 66 based on the operation of pressure switches 64A and 64B during the learn breathing routine and previous breathing cycles. The delay between the activation of the electrode pairs simulates manual activation of different muscles during the breathing cycle. In one preferred embodiment, the predetermined delay (x) is 100 ms, with pulsing of the lower back electrode pair 24A–24B occurring 100 ms after the start of anal zone electrode pair 22A–22B, and pulsing of the upper back electrode pair 26A–26B occurring 100 ms after the start of the lower back electrode pair. However, the delay (x) could have other values for example, 50 ms to 150 ms, and could be variable either through manual input, or calculated by the CPU 66 as a percentage of the measured breathing cycle. Breathing cycle mode assists in training the user to take long and deep breaths as stimulation occurs only during inhalation, thus providing feedback to the user while they are inhaling.

As indicated above, the amplitude of the applied voltage pulses to the electrode pairs 22A–22B, 24A–24B and 26A–26B is variable based on what fraction of a maximum possible voltage amplitude (as determined by thumbwheel 58 and range selector switch 56) has been selected by the user of the device 10 via the respective intensity selector switches 40, 42 and 43. During step 100-4, the CPU 66 monitors these switches, and will adjusts the digital potentiometers 78, 80 and 82 accordingly. In one preferred embodiment, as illustrated in FIG. 8, the CPU 66 is configured to cause the pulses occurring at the start of the waveforms 110, 112 and 114 to ramp up in value, maintain a selected amplitude, and then ramp down in value at the end of the waveforms 110, 112 and 114 (through adjustment of the digital potentiometers 78, 80 and 82). Such ramping up and down softens the changes in tissue stimulation that occurs during use of the device but is not necessary for all embodiments of the invention.

When they are applying voltage, the electrodes are preferably providing pulses with a frequency of up to 100 Hz when "Low" intensity has been selected and up to 250 Hz when "high" intensity has been selected, although other values are possible. In one embodiment, the CPU 66 is configured to vary the frequency of the pulses of waveforms 110,112 and 114 while the waveforms are being generated, thus exposing the body tissues to variations in pulse frequency.

The CPU 66 is configured to continue running the selected mode for a treatment period corresponding to the amount of time selected by time selector switch 54. If the repeat button 46 is pressed (step 100-6), the CPU 66 will re-commence the latest program mode it just ran using the latest settings for treatment time and intensity.

Figure 9:
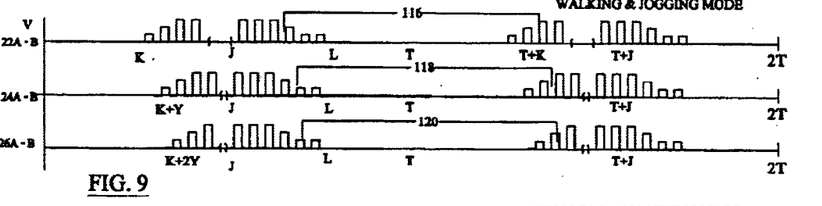
FIG. 9 is a graph showing stimulation signals generated by the electrical stimulation device during a second mode of operation in accordance with embodiments of the present invention.

In jogging and walking mode and abdominal breathing mode, the stimulation device 10 functions in a similar manner as in lung breathing mode, except for the differences noted below. FIG. 9 is illustrative of the voltage waveforms applied to the three electrode pairs 22A–22B, 24A–24B and 26A–26B during step 100-4 in the event that "exercise mode" has been selected by the user. In jogging and walking mode, the control unit 18 is configured to apply a low frequency voltage pulse waveform to each of the electrode pairs for predetermined durations commencing at predetermined times after the start of the inhalation portion of the breathing cycle, and ending at a predetermined time prior to the end of the exhalation portion. In particular, the CPU 66 is configured to, after an interval of K seconds after the calculated inhalation start time of the person 12, start pulsing the gate of the transistor Q1 that is associated with the anal zone electrode pair 22A–22B to cause stimulating electrical pulses to be applied through the anal zone electrode pair 22A–22B to the anal zone area of the person 12, as indicated by illustrative waveform 116. The CPU 66 is configured to continue sending the pulses to the electrode pair 22A–22B until a predetermined time prior to the end of the exhalation portion, namely L seconds after the calculated inhalation start time. In one preferred embodiment, the active pulsing duration of the waveform 116, namely L minus K, is selected by the CPU 66 to be equal to 75% of the duration T of the breathing cycle, with K being ⅛th of T and T minus L being ⅛th of T.

As indicated in FIG. 9, in jogging and walking mode the CPU 66 is configured to start pulsing, at a predetermined delay (y) after commencing pulsing of the anal zone electrode pair 22A–22B, the gate of the transistor Q2 that is associated with the lower back electrode pair 24A–24B to cause stimulating electrical pulses to be applied through the lower back zone electrode pair 24A–24B to the lower back/spine area of the person 12, as illustrated by the waveform 118. The CPU 66 is configured to continue sending the pulses to the electrode pair 24A–24B until a predetermined time prior to the end of the exhalation portion, namely L seconds after the calculated inhalation start time. The CPU 66 is also configured to start pulsing, at a predetermined delay (y) after commencing pulsing of the lower back zone electrode pair 24A–24B, the gate of the transistor Q3 that is associated with the upper back electrode pair 26A–26B to cause stimulating electrical pulses to be applied through the upper back electrode pair 26A–26B to the upper back/spine area of the person 12, as illustrated by the waveform 120. The CPU 66 is configured to continue sending the pulses to the electrode pair 26A–26B until a predetermined time prior to the end of the exhalation portion, namely L seconds after the calculated inhalation start time.

Thus, in jogging and walking mode, during each breathing cycle, the anal zone electrode pair 22A–22B is activated after a predetermined delay from the start of inhalation, followed after a further predetermined delay by the lower back electrode pair 24A–24B, followed after yet a further predetermined delay by the upper back electrode pair 26A–26B, with stimulating pulses from all three electrode pairs continuing through the remainder of inhalation and ceasing prior to the end of exhalation, with the inhalation and exhalation start times being determined by the CPU 66 based on the operation of pressure switches 64A and 64B during the learn breathing routine and previous breathing cycles. In one preferred embodiment, the predetermined delay (y) is 200 ms, with pulsing of the lower back electrode pair 24A–24B occurring 200 ms after the start of anal zone electrode pair 22A–22B, and pulsing of the upper back electrode pair 26A–26B occurring 200 ms after the start of the lower back electrode pair 24A–24B. However, the delay (y) could have other values, and could be variable either through manual input, or calculated by the CPU 66 as a percentage of the measured breathing cycle.

Figure 10:
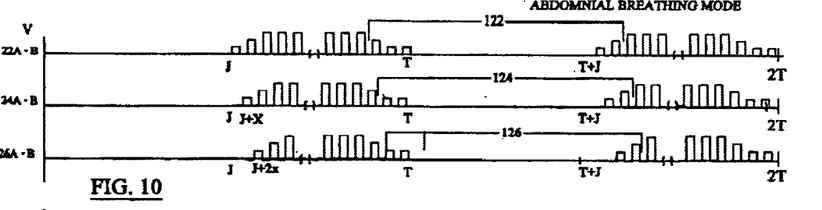
FIG. 10 is a graph showing stimulation signals generated by the electrical stimulation device during a third mode of operation in accordance with embodiments of the present invention.

FIG. 10 is illustrative of the voltage waveforms applied to the three electrode pairs 22A–22B, 24A–24B and 26A–26B during step 100-4 in the event that "abdominal breathing mode" has been selected by the user. In abdominal breathing mode, the control unit 18 is configured to apply a low frequency voltage pulse waveform to each of the electrode pairs for predetermined durations during the exhalation portion of the breathing cycle. In particular, the CPU 66 is configured to, at the calculated exhalation start time of the person 12, start pulsing the gate of the transistor Q1 that is associated with the anal zone electrode pair 22A–22B to cause stimulating electrical pulses to be applied through the anal zone electrode pair 22A–22B to the anal zone area of the person 12, as indicated by illustrative waveform 122. The CPU 66 is configured to continue sending the pulses to the electrode pair 22A–22B throughout exhalation and then cease at the end of the exhalation portion of the breathing cycle.

As indicated in FIG. 10, in abdominal breathing mode the CPU 66 is configured to start pulsing, at a predetermined delay (x) after commencing pulsing of the anal zone electrode pair 22A–22B, the gate of the transistor Q2 that is associated with the lower back electrode pair 24A–24B to cause stimulating electrical pulses to be applied through the lower back zone electrode pair 24A–24B to the lower back/spine area of the person 12, as illustrated by the waveform 124. The CPU 66 is configured to continue sending the pulses to the electrode pair 24A–24B throughout the rest of the exhalation portion and then cease at the end of the exhalation portion of the breathing cycle. The CPU 66 is also configured to start pulsing, at a predetermined delay (x) after commencing pulsing of the lower back zone electrode pair 24A–24B, the gate of the transistor Q3 that is associated with the upper back electrode pair 26A–26B to cause stimulating electrical pulses to be applied through the upper back electrode pair 26A–26B to the upper back/spine area of the person 12, as illustrated by the waveform 126. The CPU 66 is configured to continue sending the pulses to the electrode pair 26A–26B throughout the rest of the exhalation portion and then cease at the end of the exhalation portion of the breathing cycle.

Thus, in abdominal breathing mode, during each breathing cycle, the anal zone electrode pair 22A–22B is activated commencing at the start of exhalation, followed after a predetermined delay by the lower back electrode pair 24A–24B, followed after a further predetermined delay by the upper back electrode pair 26A–26B, with stimulating pulses from all three electrode pairs continuing through the remainder of exhalation and ceasing at the end of exhalation, with the exhalation start and end times being determined by the CPU 66 based on the operation of pressure switches 64A and 64B during the learn breathing routine and previous breathing cycles. In one preferred embodiment, the predetermined delay (x) is 100 ms, with pulsing of the lower back electrode pair 24A–24B occurring 100 ms after the start of anal zone electrode pair 22A–22B, and pulsing of the upper back electrode pair 26A–26B occurring 100 ms after the start of the lower back electrode pair. However, the delay (x) could have other values, and could be variable either through manual input, or calculated by the CPU 66 as a percentage of the measured breathing cycle.

Electrical stimulation of the nerves in the anal area, followed by subsequent stimulation of nerves along the spine in the lower back area, followed by subsequent stimulation of nerves along the spine in the upper back area, done in a consistent manner during breathing cycles over a duration of time can promote relaxation and well being in the user of the electrical device 10. Use of the present device can train the user to practice deep breathing by encouraging the user to concentrate on long inhalations and exhalations by providing electrical feedback at different times during the breathing cycle depending on the mode selected. Lung breathing mode is intended to be used to train the user to expand their lung capacity, which in turn benefits the body due to increased volumes of oxygen being introduced in the blood stream. Some doctrines, including Taoism and Yoga, advocate deep breathing meditation as a method for purifying the body from toxins. Use of the device in walking and jogging mode, and in particular tensing of the anal area caused by the electrical stimulation, is intended to prevent the escape of energy from the body to help re-energize body strength and improve health. Abdominal mode is intended to assist the user in achieving what is known in Tao meditation as "bone marrow wash", which is believed to stimulate the spinal chord and improve the immune system. Abdominal mode also is intended to train the user to activate what is known as Chakras (energy centres) in Yoga, in order to keep the flow of information between the brain and other parts of the body flowing freely.

Figure 11:
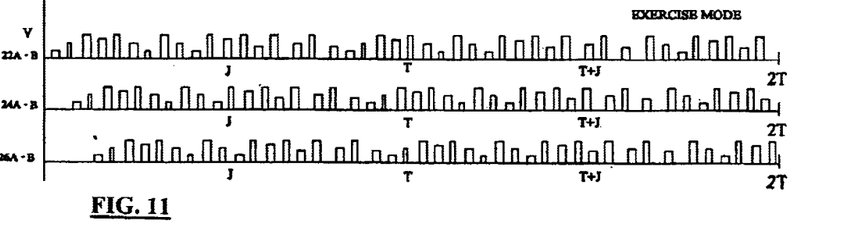
FIG. 11 is a graph showing stimulating signals generated by the electrical stimulation device during a fourth mode of operation in accordance with embodiments of the present invention.

FIG. 11 is illustrative of the voltage wave forms applied to the three electrode pairs 22A–22B, 24A–24B and 26A–26B in the event that "exercise mode" has been selected by the user. In exercise mode, the CPU 66 is configured to apply pulses of randomly varying frequency (50–180 Hz on one embodiment) and randomly varying amplitude to three electrode pairs continuously throughout the treatment time. In one embodiment, the pulsing of the electrode pairs is periodically ceased and then restarted during treatment time in order to provide a reminder to the user to focus on proper breathing and meditation techniques during the treatment time. For example, the pulsing may continue for 2 minutes, then cease for 30 seconds, then restart for 2 minutes, and so on, throughout the treatment time. In exercise mode, the breathing pattern of the user need not be measured, as the pulses are applied irrespective of the breathing cycles. As indicated in FIG. 11, there may be predetermined delays between activation of the anal zone electrodes, lower back zone electrodes, and upper back zone electrodes at the start-up of the treatment time. Exercise mode is intended to generally confine energy in the body to help promote the user's health.

The fifth possible mode of operation of the present invention is "Meditation Mode", which is selected through the Meditation Mode switch 59. In meditation mode, the control unit progresses successively through lung breathing mode, abdominal breathing mode and exercise breathing mode for the duration of the treatment time. For example, if the treatment time of 15 minutes is selected, the control unit 18 will perform approximately three and a half minutes of each lung and abdominal breathing mode, then 9 minutes of exercise mode. If the treatment time is 20 minutes, then the unit will perform about four minutes each of Lung and Abdominal Mode, followed by 12 minutes of exercise mode. If the treatment time is 25 minutes, then the unit will perform about 5 minutes each of lung and Abdominal mode, followed by 15 minutes of exercise mode. Meditation mode is intended for use by persons who have mastered the lung, abdominal and exercise modes independently, in order to provide the benefits of these three modes.

In addition to encouraging the user to learn proper meditative breathing, the stimulation provided under the different operational modes of the present invention are intended to stimulate the anal and spinal areas in a manner consistent with some eastern meditative doctrines (such stimulation traditionally being done by precisely timed self-activation of muscles by a highly trained meditation practitioner), thus permitting less skilled meditative practitioners to experience the same benefits previously available only to highly experienced and skilled practitioners.

It will be appreciated that the electrical stimulation device 10 described above could be modified in many respects and still perform the same functions. For example, other pressure sensitive devices, such as strain gauges, could be used instead in sensor units 20 in place of switches 64A and 64B, and the number of sensor units varied. Characteristics other than expansion of the body torso could be used to determine breathing patterns—for example, a microphone or airflow sensor could be used to detect breath entering and exiting the mouth of person 12. In some applications, the number of and/or location of electrode pairs could be varied as well. Although the control unit 18 has been shown as a central control unit implemented using a programmed CPU, it could be implemented using other electronic configurations such as programmable logic circuits or dedicated electronic components such as ASICs, or combinations thereof. Rather than be localized in a single housing, elements of the control unit 18 could be distributed with greater functionality occurring at the sensor units 20, for example.

While particular embodiments of the invention have been shown and described, it will be obvious to those skilled in the art that various changes and modifications may be made without departing from the present invention in its broader aspects.

What is claimed is:

1. An electrical stimulation device for applying electrical stimulation to living tissue, comprising:

an elongate member for securing to a person's body;

a plurality of electrode pairs arranged along the elongate member for applying stimulating electrical pulses along an anal area and a spinal area of the person's body;

a sensing device for sensing breathing of the person; and a controller connected to receive signals from the sensing device and control operation of the electrode pairs for the controller configured for generating the stimulating electrical pulses and causing the electrode pairs to apply the stimulating electrical pulses along the anal area and the spinal area based on signals received from the sensing device.

2. An electrical stimulation device for applying a stimulation signal to living tissue, comprising:

a sensor for sensing breathing of a person;

at least a first electrode pair and a second electrode pair for contacting the living tissue of the person; and a controller responsive to the sensor and operatively connected to the first electrode pair and the second electrode pair for determining a breathing cycle pattern of the person based on input from the sensor and generating a stimulating first waveform and a stimulating second waveform for application to the living tissue through the first electrode pair and the second electrode pair, respectively, based on the determined breathing cycle pattern of the person, the controller being configured to generate the first waveform signal and the second waveform signal, respectively, for predetermined durations during each breathing cycle of the person during a treatment period, the controller being configured to commence the second waveform signal a predetermined delay after commencement of the first waveform signal in each breathing cycle, wherein the first electrode pair is adapted to be applied to an anal area of the person, and the second electrode pair is adapted to be applied higher than the first electrode pair to a lower spine area of the person.

3. The electrical stimulation device of claim 2 wherein the controller is configured to determine, based on the determined breathing cycle pattern, a calculated inhalation period and the controller is configured to operate in a mode during which the first waveform signal and the second waveform signal are generated only during the calculated inhalation period for each breathing cycle during the treatment period.

4. The electrical stimulation device of claim 2 wherein the controller is configured to determine, based on the determined breathing cycle pattern, a calculated inhalation period and a calculated exhalation period and the controller is configured to operate in a mode in which the first waveform signal and the second waveform signal are generated for respective durations that commence during the calculated inhalation period and end during the calculated exhalation period for each breathing cycle during the treatment period.

5. The electrical stimulation device of claim 2 wherein the controller is configured to determine, based on the determined breathing cycle pattern, a calculated exhalation period and the controller is configured to operate in a mode in which the first waveform signal and the second waveform signal are generated only during the calculated exhalation period for each breathing cycle during the treatment period.

6. The electrical stimulation device of claim 2 wherein the controller is configured to accept user input as to a desired timing of the first and second waveform occurrences within the determined breathing cycle pattern, and adjust the timing accordingly.

7. The electrical stimulation device of claim 2 including an elongate member wherein said first and second electrode pairs are arranged along the elongate member to assist in correct placement of the electrode pairs on the person.

8. The electrical stimulation device of claim 7 further including a third electrode pair connected to the controller, the controller being configured for generating a stimulating third voltage waveform for application to the living tissue of the person through the third electrode pair, the third electrode being arranged on the elongate member so as to be located on an upper back area of the person higher than the second electrode pair, the controller being configured to generate the third waveform signal to the living tissue for a predetermined duration during each determined breathing cycle of the person during the treatment period, the third waveform signal commencing a predetermined delay after commencement of the second waveform signal in each breathing cycle.

9. The electrical stimulation device of claim 2 including a belt wherein the sensor includes at least two pressure sensing devices mounted on the belt, the belt and sensing devices being configured such that the sensing devices can detect expansion and contraction of the person's torso during breathing when the belt is worn about the person's torso.

10. The electrical stimulation device of claim 2 wherein the controller is configured to operate in a mode during which the controller varies the first waveform and the second waveform throughout a treatment time.

11. The electrical stimulation device of claim 2 wherein the controller includes user input means for allowing the person to select a desired intensity of the signals applied to the first and second electrode pairs, the controller being configured to adjust an intensity of the signals accordingly.

12. The electrical stimulation device of claim 11 wherein the user input means includes a range selector for selecting one of a plurality of possible signal intensity ranges, and a further selector for selecting signal intensities within the selected signal intensity range.

13. An electrical stimulation device for applying a stimulation signal to living tissue, comprising:

a sensor for sensing breathing of a person;

at least a first electrode pair and a second electrode pair for contacting the living tissue of the person; and a controller responsive to the sensor and operatively connected to the first electrode pair and the second electrode pair for determining a breathing cycle pattern of the person based on input from the sensor and generating a stimulating first waveform and a stimulating second waveform for application to the living tissue through the first electrode pair and the second electrode pair, respectively, based on the determined breathing cycle pattern of the person, wherein the first electrode pair is adapted to be applied to an anal area of the person, and the second electrode pair is adapted to be applied higher than the first electrode pair to a lower back of the person.

* * * * *